United States Patent
Bor et al.

(10) Patent No.: US 7,323,584 B2
(45) Date of Patent: Jan. 29, 2008

(54) PROCESS FOR PREPARING N-(4'-CYANO-3'-TRIFLUOROMETHYL-PHENYL)-3-(4"-FLUOROPHENYLSULFO-NYL)-2-HYDROXY-2-METHYLPROPIONA-MIDE

(75) Inventors: Ádám Bor, Budaörs (HU); György Orosz, Budapest (HU); Ferenc Lukács, Kistarcsa (HU); Géza Schneider, Budapest (HU)

(73) Assignees: Helm AG, Hamburg (DE); CF Pharma Gyogyszergyarto KFT, Budapest (HU)

( * ) Notice: Subject to any disclaimer, the term of this patent is extended or adjusted under 35 U.S.C. 154(b) by 261 days.

(21) Appl. No.: 10/498,862

(22) PCT Filed: May 13, 2003

(86) PCT No.: PCT/EP03/04999

§ 371 (c)(1),
(2), (4) Date: Oct. 8, 2004

(87) PCT Pub. No.: WO03/097590

PCT Pub. Date: Nov. 27, 2003

(65) Prior Publication Data

US 2005/0033082 A1     Feb. 10, 2005

(30) Foreign Application Priority Data

May 17, 2002   (DE) ................. 102 22 104

(51) Int. Cl.
*C07C 255/50*   (2006.01)
*C07C 69/76*    (2006.01)

(52) U.S. Cl. .......................... 558/413; 560/8

(58) Field of Classification Search ................ 558/413; 560/8
See application file for complete search history.

(56) References Cited

U.S. PATENT DOCUMENTS

2003/0073742 A1    4/2003   Thijs et al.

FOREIGN PATENT DOCUMENTS

| DE | 3304054 | 8/1984 |
| DE | 41 05 743 C1 | 10/1992 |
| EP | 0 279 162 A1 | 8/1988 |
| WO | WO 01/00608 | 1/2001 |
| WO | WO 01/28990 | 4/2001 |

OTHER PUBLICATIONS

Culvenor, C.C.J. et al., "Some Reactions of Arylsulphonylpropane Derivatives," *J. Chem. Soc.*, pp. 2198-2206 (1949).
Derwent English Language Abstract of DE 3304054 (Document B3, above).
Klamann, D. (ed.), "Methoden der organischen Chemie (Houben-Weyl), Band E11 Organische Schwefel-Verbindungen," pp. 1145-1150, George Thieme Verlag (Stuttgart 1985).
Patent Abstract of Japan, Publication No. 2001-213860, Oct. 1, 1992.
DERWENT English language abstract of DE 41 05 743 C1. (Document B4 above.), Oct. 1, 1992.
DERWENT English language abstract of EP 0 279 162 A1. (Document B5 above.), Aug. 24, 1988.

*Primary Examiner*—James O. Wilson
*Assistant Examiner*—Ebenezer Sackey
(74) *Attorney, Agent, or Firm*—Bryan Cave LLP

(57) ABSTRACT

The invention relates to a process for preparing N-(4'-cyano-3'-trifluoromethylphenyl)-3-(4"-fluorophenylsulfonyl)-2-hydroxy-2-methylpropionamide (bicalutamide).

9 Claims, No Drawings

PROCESS FOR PREPARING N-(4'-CYANO-3'-TRIFLUOROMETHYL-PHENYL)-3-(4''-FLUOROPHENYLSULFO-NYL)-2-HYDROXY-2-METHYLPROPIONAMIDE

This application is the National Stage of International Application No. PCT/EP03/04999, filed May 13, 2003.

The present invention relates to a process for preparing (±)-N-(4'-cyano-3'-trifluoromethylphenyl)-3-(4''-fluorophenylsulfonyl)-2-hydroxy-2-methylpropionamide and its R-(−) and S-(+) enantiomers.

N-(4'-Cyano-3'-trifluoromethylphenyl)-3-(4''-fluorophenylsulfonyl)-2-hydroxy-2-methylpropionamide is also known under the INN name bicalutamide and belongs to the class of acylanilides. Bicalutamide has the following chemical structural formula:

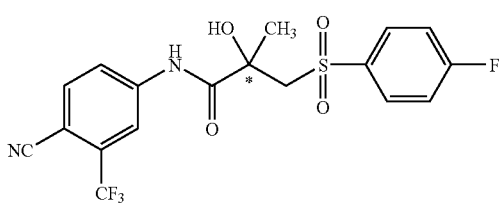

The compound has an asymmetric C atom (*) and can therefore exist both in its racemic form as (±)-bicalutamide and as R-(−) or S-(+) enantiomer.

Numerous acylanilides have antiandrogenic properties and are currently referred to as non-steroidal, peripheral antiandrogens. These compounds are suitable for the therapy of androgen-related diseases such as, for example, benign or malignant disorders of the prostate, hirsutism, acne etc.

Bicalutamide has been marketed in the form of its racemate under the proprietary name Casodex® as remedy for prostate carcinomas since 1995.

Acylanilides having antiandrogenic properties, which also include bicalutamide, are disclosed for example in EP 0 100 172. This document also describes various synthetic routes which, applied to bicalutamide, can be summarized as follows:

In a first synthetic route starting from methyl methacrylate, firstly an epoxide is prepared, that is opened by an addition reaction with p-fluorothiophenol. After an ester cleavage, the corresponding amide is formed and, in the last step, the sulfide is oxidized to the sulfone using a peracid such as m-chloroperbenzoic acid (m-CPBA). This synthetic route is illustrated by the following reaction scheme:

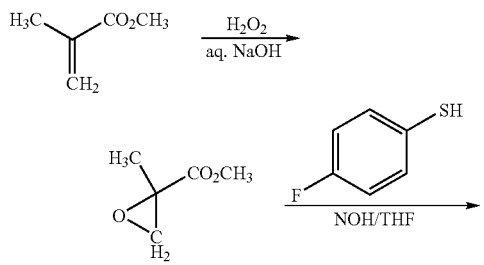

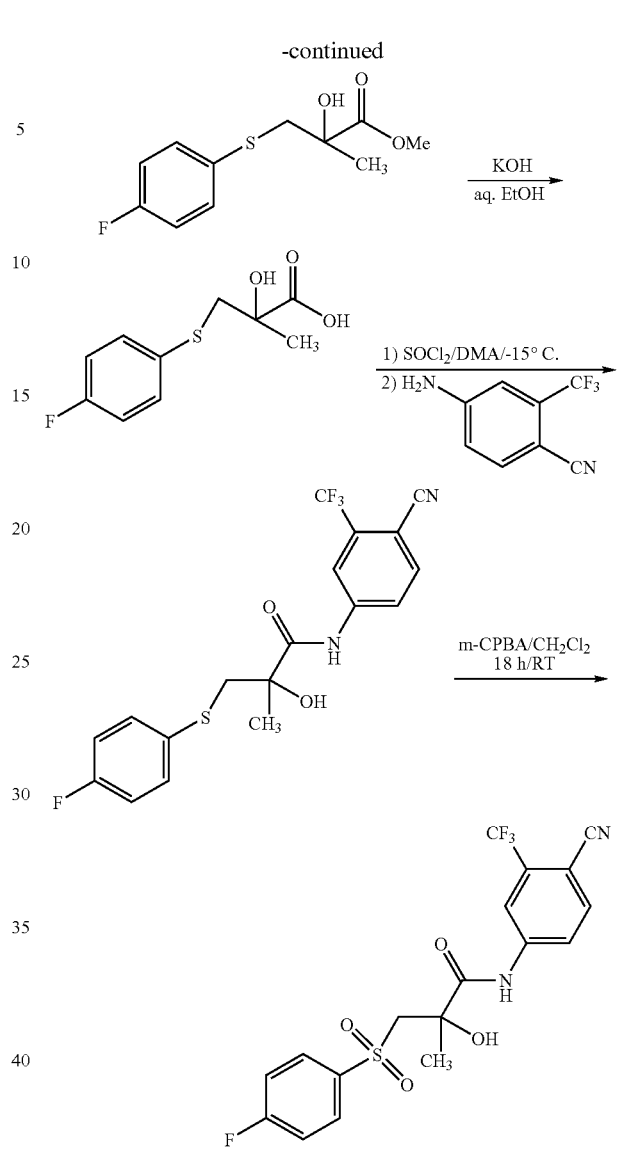

In a second reaction route starting from bromoacetone, firstly the corresponding sulfide is formed with p-fluorothiophenol, and the acid is then introduced therein via a cyanohydrin reaction. After amide formation with 3-trifluoromethyl-4-cyanoaniline, in the last step the sulfide is then again oxidized to the sulfone. This synthetic route is illustrated by the following reaction scheme:

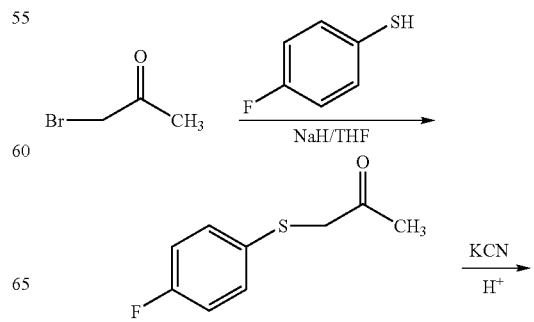

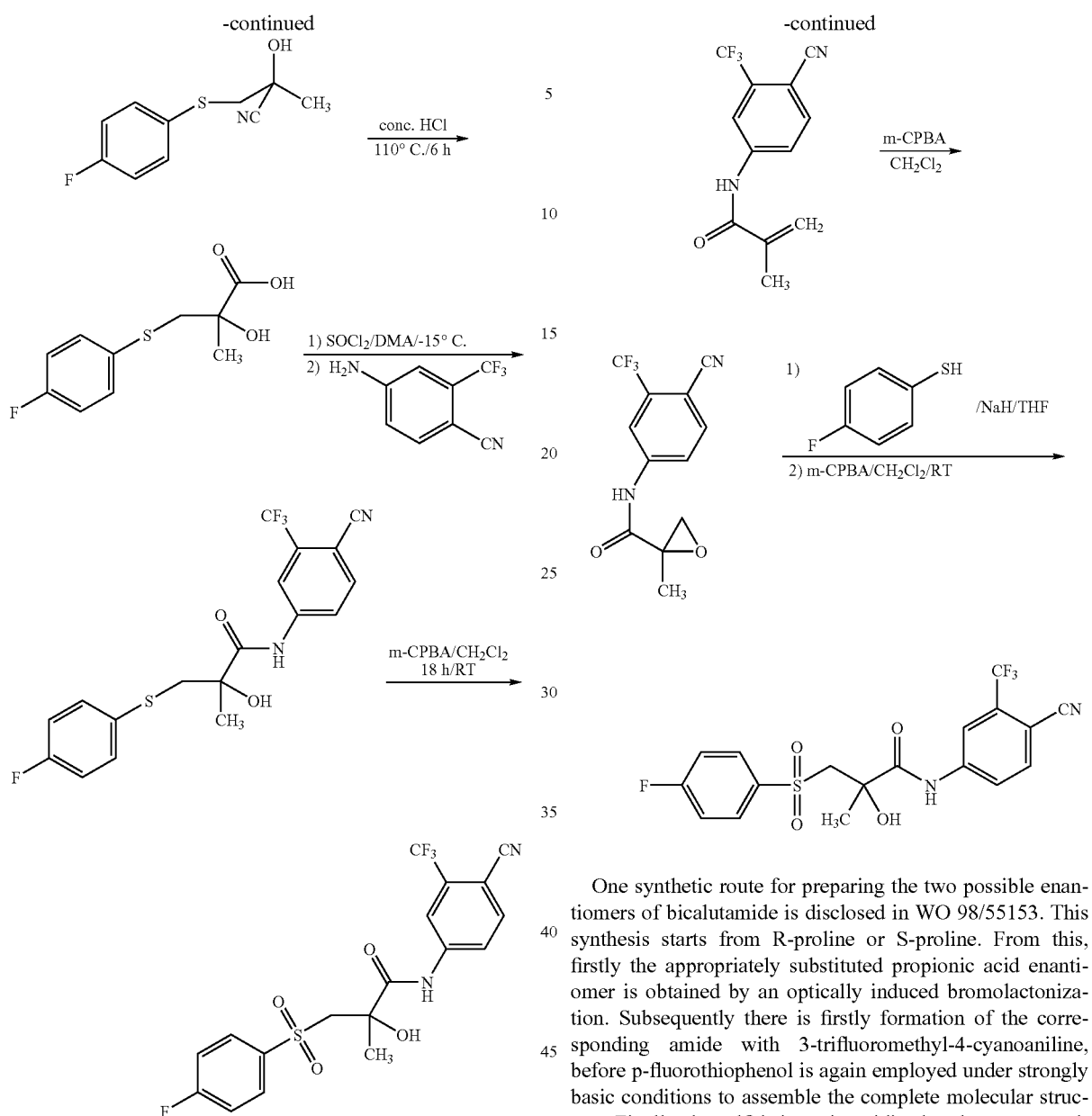

In a further synthetic route disclosed in EP 0 100 172 there is firstly formation from methacryloyl chloride with 3-trifluoromethyl-4-cyanoaniline of the corresponding amide, which is then converted into an oxirane. The latter is opened by an addition reaction with p-fluorothiophenol and finally the sulfide is again oxidized to the sulfone. This reaction route is illustrated by the following reaction scheme:

One synthetic route for preparing the two possible enantiomers of bicalutamide is disclosed in WO 98/55153. This synthesis starts from R-proline or S-proline. From this, firstly the appropriately substituted propionic acid enantiomer is obtained by an optically induced bromolactonization. Subsequently there is firstly formation of the corresponding amide with 3-trifluoromethyl-4-cyanoaniline, before p-fluorothiophenol is again employed under strongly basic conditions to assemble the complete molecular structure. Finally, the sulfide is again oxidized to the corresponding sulfone. This reaction route applied to R-(−)-bicalutamide is illustrated by the following reaction scheme:

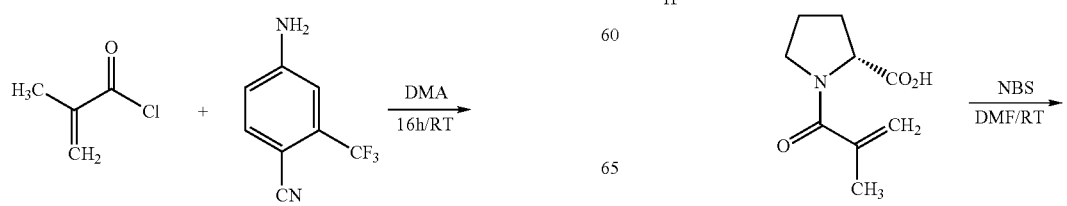

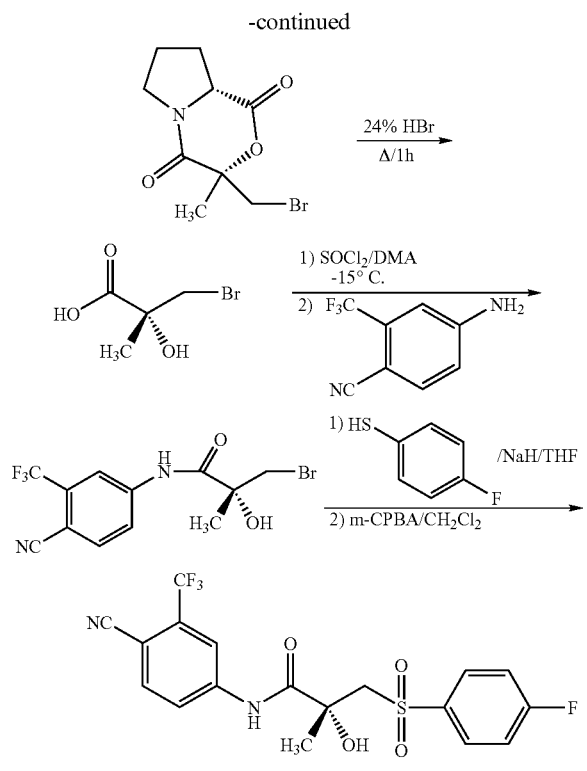

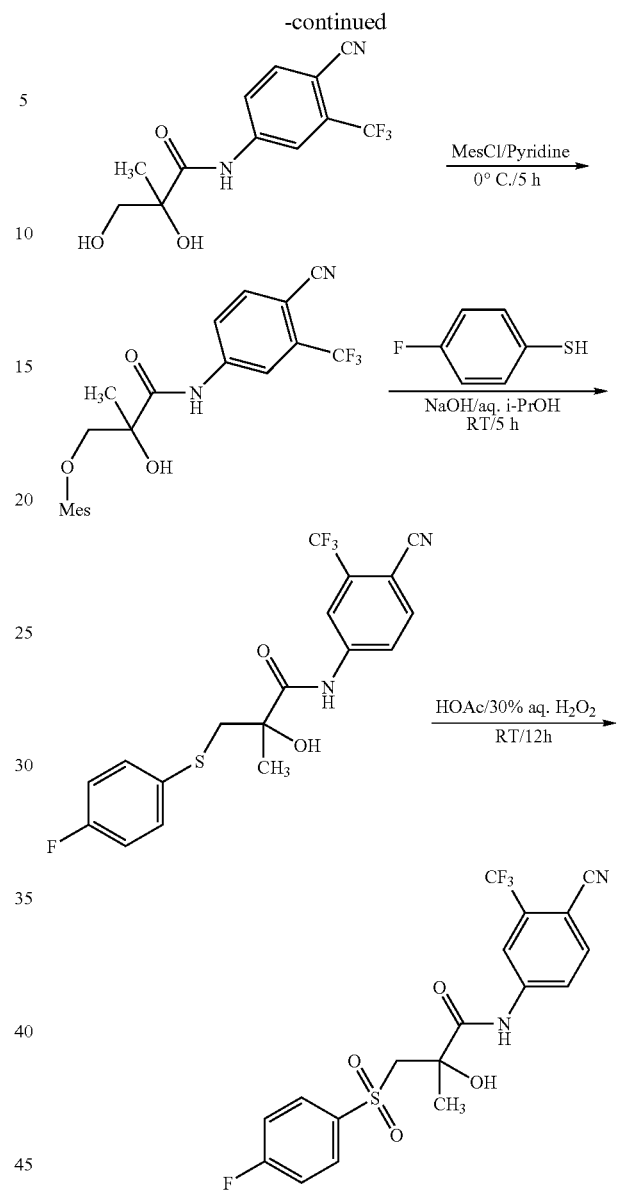

A further alternative process for preparing bicalutamide is described in WO 01/00608. This process starts from 2,3-dihydroxy-2-methylpropionic acid and, during the process, likewise reacts with 3-trifluoromethyl-4-cyanoaniline to give the corresponding amide and finally with p-fluorothiophenol to give the corresponding sulfide. The latter is subsequently oxidized to the desired sulfone. This synthesis is illustrated by the following reaction scheme:

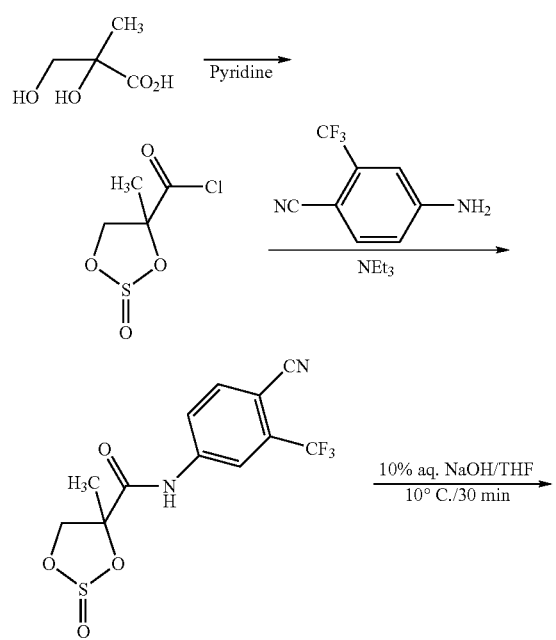

Finally, WO 01/28990 discloses a process for the asymmetric synthesis of an enantiomer of an acylanilide by opening a cyclic structure. In the examples, bicalutamide is prepared by reaction with p-fluorothiophenol and subsequent oxidation of the resulting sulfide to the corresponding sulfone using m-chloroperbenzoic acid.

All the prior art processes described above use the following reaction steps in principle for preparing bicalutamide:

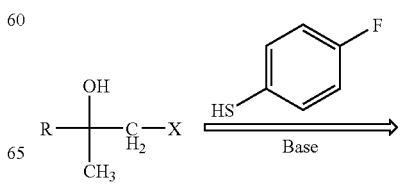

-continued

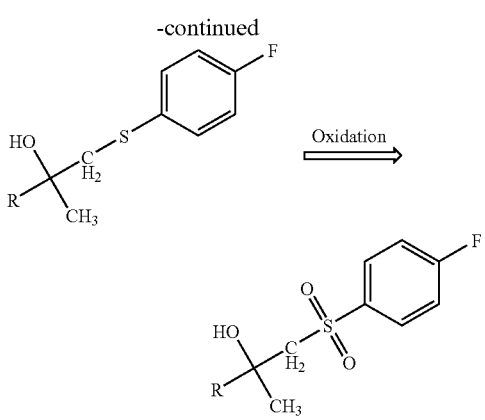

where R is the respective remaining moiety of the bicalutamide structure or of an appropriate precursor, and X either is a conventional leaving group such as, for example, Cl, Br, I, MesO, TosO etc., or forms together with the C atom in the α position an appropriate epoxide which then undergoes addition of p-fluorothiophenol under basic conditions to give a sulfide which is oxidized in the next step to the corresponding sulfone. As is evident from the examples shown, this reaction sequence need not occur at the end of a bicalutamide synthesis, but may also be used in the middle of the reaction sequence. Likewise, the oxidation need not necessarily follow directly on the formation of the sulfide, but can also be carried out later. Both individual steps are, however, used in all bicalutamide syntheses.

The use of p-fluorothiophenol and the consequent need to oxidize the sulfide which is formed to the desired sulfone exhibits numerous disadvantages, however. Firstly, p-fluorothiophenol is a toxic and highly irritant material which makes appropriate precautions necessary in order to be able to utilize this compound on the industrial scale. Secondly, p-fluorothiophenol can be obtained in isomerically pure form only with difficulty. A corresponding purification is complicated. Thirdly, a strong base is needed for the addition reaction of the p-fluorothiophenol. Most synthetic processes use sodium hydride, but this makes it necessary to employ absolute solvents and makes management of the reaction on the industrial scale difficult owing to the very great sensitivity to hydrolysis. The use of weaker bases requires the additional step of introducing a reactive leaving group. Fourthly, a strong oxidizing agent must be employed to oxidize the sulfide to the sulfone. The oxidizing agents described in the prior art mentioned were m-chloroperbenzoic acid, mixtures of $H_2O_2$ with organic acids and Oxone® (2 $KHSO_5 \cdot KHSO_4 \cdot K_2SO_4$ salt).

However, m-chloroperbenzoic acid is relatively costly, mixtures of $H_2O_2$ with organic acids lead to peracids which are hazardous to handle on the industrial scale, and the use of Oxone® requires the use of phase transfer conditions, which are industrially complicated, to achieve acceptable yields.

There is thus a continuing need for an economic process which can be carried out simply for preparing bicalutamide, which preferably provides bicalutamide either in racemic or in enantiopure form. In addition, the purity of the resulting bicalutamide ought where possible to be that necessary for use in medicaments.

One object of the present invention is thus to provide a process for preparing bicalutamide which overcomes the aforementioned disadvantages.

It has now surprisingly been found that bicalutamide can be obtained in a simple manner even without use of p-fluorothiophenol and the correspondingly necessary oxidation of the resulting sulfide to the sulfone by means of a reaction of an epoxide or of an epoxide precursor with a p-fluorophenylsulfinate salt.

The present invention thus relates to a process for preparing bicalutamide in which an epoxide of the general formula (I)

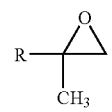

in which R is a radical of the formula (II)

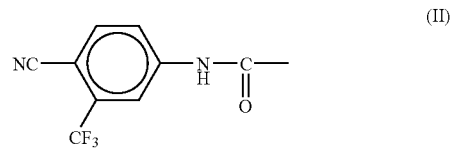

(II)

or a precursor thereof is reacted with a p-fluorophenylsulfinate salt and, if R is a precursor of the radical of the formula (II), the latter is converted into a radical of the formula (II).

This reaction is illustrated by the following reaction scheme involving a reaction with the preferred sodium p-fluorophenylsulfinate:

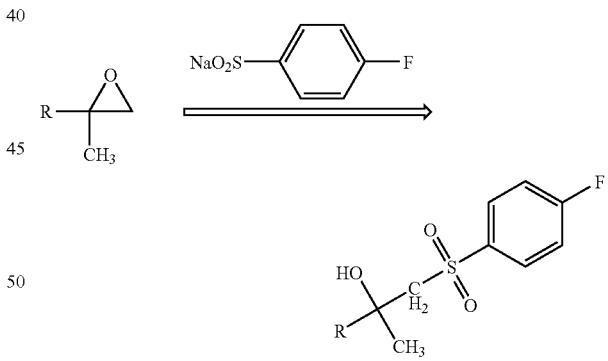

An alternative possibility is to employ in place of the epoxide in the process of the invention an epoxide precursor, namely a compound of the general formula (III)

(III)

in which R is as defined above, and X is a leaving group.

The process of the invention thus avoids the use of the toxic p-fluorothiophenol and the need for an oxidation step through the use of a p-fluorophenylsulfinate as epoxide-opening reagent. In this way, the desired product bicalutamide, or a precursor thereof which, however, already contains the desired sulfone group, is obtained directly.

The epoxide of the general formula (I) can either be employed as starting material in the process of the invention or be obtained by a ring-closure reaction from a compound of the general formula (III)

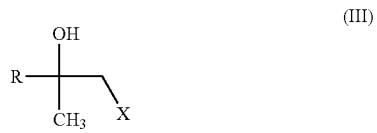

(III)

in which R is as defined above, and X is a leaving group. If desired, the epoxide obtained as intermediate can be isolated and purified, but the reaction is preferably continued as one-pot reaction without isolation of the epoxide. This reduces the expenditure of time and effort and thus the costs of the synthesis and nevertheless makes it possible to obtain the desired bicalutamide in adequate purity. An alternative possibility is, as already stated above, to react the compound of the general formula (III), without intermediate oxirane formation, directly with the p-fluorophenylsulfinate salt.

The epoxide employed in the process of the invention, or its open-chain precursor, is preferably chosen so that the desired bicalutamide is obtained directly in the reaction with the p-fluorophenylsulfinate. In this case, R in the general formulae (I) and (III) is a radical of the formula (II)

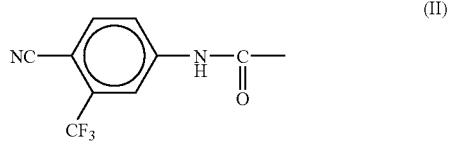

(II)

The reaction according to the invention of the epoxide with the p-fluorophenylsulfinate salt need, however, not necessarily be at the end of the synthetic route for preparing bicalutamide. It is therefore also possible for R in the general formulae (I) and (III) to be chosen so that the product obtained in the reaction from the epoxide with p-fluorophenylsulfinate salt is suitable as precursor for further synthesis of bicalutamide. For this purpose, R is chosen so that R serves as precursor for a radical of the formula (II)

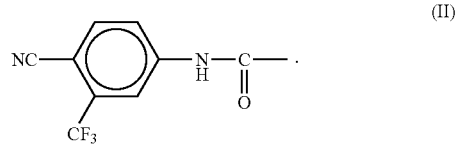

(II)

An example of a suitable precursor for a radical of the formula (II) is the radical —COY in which Y is a group suitable for the subsequent amide formation. In this case, the intermediate obtained in the reaction of the epoxide with the p-fluorophenylsulfinate salt can easily be reacted further with 3-trifluoromethyl-4-cyanoaniline to give the desired bicalutamide. Particularly suitable precursors for a radical of the formula (II) are carboxyl, acid halides such as acid chloride, normal esters and activated esters. Suitable radicals are known to the skilled worker and can be chosen to be appropriate for the management of the reaction.

If the process of the invention starts not from an epoxide of the general formula (I) but from a precursor thereof, namely a compound of the general formula (III)

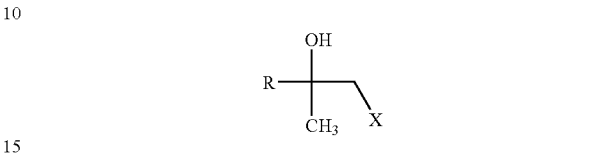

the leaving group X can be chosen by the skilled worker to be appropriate for the chosen reaction conditions. Suitable leaving groups are know to the skilled worker and include halogens such as, for example, Cl, Br and I, and reactive leaving groups such as, for example, alkyl- and arylsulfonates and in particular, mesylate, tosylate and brosylate.

Suitable starting materials in which X is a halogen have been disclosed for example in WO 98/55153 or can be prepared simply from the epoxide precursor by conventional processes of organic chemistry.

Suitable starting materials in which X is a common leaving group such as, for example, a mesylate, brosylate or tosylate group are disclosed in WO 01/00608 and can be obtained from the corresponding alcohol precursor by conventional processes of organic chemistry.

If the epoxide is to be employed, in place of the epoxide precursor, in the process of the invention, it can be obtained for example as described in EP 0 100 172.

The p-fluorophenylsulfinate salts preferably employed according to the invention are ammonium p-fluorophenylsulfinate, alkaline earth metal p-fluorophenylsulfinates or alkali metal p-fluorophenylsulfinates and particularly preferably sodium p-fluorophenylsulfinate. The latter can be obtained in very good yield by a known route, e.g. as described by Olah, Pavlath, Acta Chim. Hung. 4 [1954] pages 111-117.

The process of the invention additionally has the advantage that the opening of the epoxide does not influence the stereochemical center already present in the epoxide, so that the process of the invention can be used both to prepare (±)-bicalutamide and to prepare R-(−)- or S-(+)-bicalutamide. The only aspect to be considered in this connection is whether the racemic epoxide or its halohydrin precursor or a corresponding optically active R- or S-epoxide or the corresponding optically active halohydrin precursor is employed as starting material. The reaction according to the invention of the epoxide with the p-fluorophenylsulfinate salt preferably takes place in a suitable solvent such as, for example, methanol or DMF, in the presence of an acid such as, for example, glacial acetic acid, at room temperature or with heating.

In a preferred embodiment of the invention, the epoxide of the general formula (I) is reacted with sodium p-fluorophenylsulfinate in a suitable solvent such as methanol after addition of glacial acetic acid with heating at about 50° C. for about 5 h. After completion of the reaction, the removal of the volatile constituents from the reaction mixture is followed by working up by an aqueous/organic extraction process. The crude product obtained after the organic solvent has been stripped off is recrystallized from a suitable solvent, e.g. from diisopropyl ether, resulting in pure bicalutamide. This reaction is illustrated by the following reaction scheme:

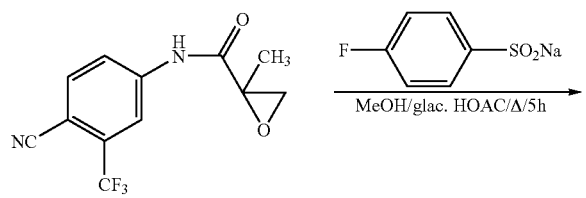

In a further preferred embodiment of the process of the invention, firstly the corresponding oxirane is generated from an open-chain compound of the general formula (III) in situ (e.g. by heating the compound of the general formula (III) with potassium tert-butoxide in toluene). In a second step, without isolating the oxirane which is formed it is then reacted in a suitable solvent such as dimethylformamide (DMF) after addition of glacial acetic acid at room temperature or slightly elevated temperature for about 16 h. This reaction is illustrated by the following scheme:

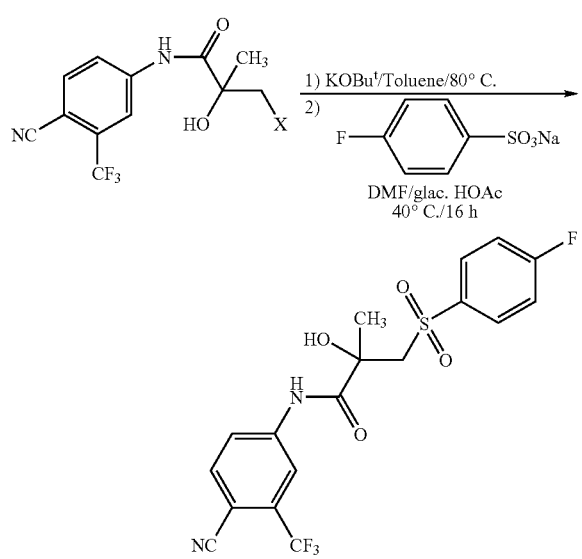

The yield of bicalutamide in the one-pot reaction is by its nature better than on isolation of the oxirane as intermediate because, for example, a normal workup loss on isolation of the oxirane is avoided. The reaction residue can be worked up for example after volatile constituents have been stripped off by taking up in dimethylformamide and diluting with water, whereupon the product crystallizes. If necessary, this can be followed by further purification by recrystallization from a suitable solvent such as, for example, diisopropyl ether.

The process of the invention is explained in more detail by the following examples:

EXAMPLE 1

Synthesis of Bicalutamide from the Epoxide Precursor 7.0 g (25.9 mmol) of N-(4'-cyano-3'-trifluoromethylphenyl)-2-methyloxirane-2-carboxamide, 9,43 g (51.8 mmol) of sodium p-fluorophenylsulfinate are introduced into 50 ml of methanol and 3 ml of glacial acetic acid in a four-neck flask and then heated under reflux for 5 hours.

After completion of the reaction, the reaction mixture is evaporated to dryness and the residue is taken up in 50 ml of $CH_2Cl_2$ and 20 ml of water. The organic phase is washed several times with water and dried over $MgSO_4$. Stripping off the solvent results in crude bicalutamide which is recrystallized from diisopropyl ether for further purification.

| Yield: | 7.1 g |
| --- | --- |
| Melting point: | 187°-189° C. |
| Purity: | 96.6% (HPLC) |

EXAMPLE 2

Synthesis of Bicalutamide from the Halohydrin Precursor (One-Pot Variant)

3.07 g of 3-chloro-N-(4'-cyano-3'-trifluoromethylphenyl)-2-hydroxypropionamide are suspended in 50 ml of toluene and heated to 80° C. Then, while stirring vigorously, 1.12 g of potassium t-butoxide in 20 ml of toluene are added over the course of 30 min. The mixture is then stirred at the same temperature for 30 min.

After cooling to room temperature, 3.64 g of sodium p-fluorophenylsulfinate, 0.6 ml of glacial acetic acid and 50 ml of DMF are added; the resulting suspension is then stirred at 40° C. for 16 h. The residue after removal of the volatile constituents in vacuo is dissolved in a little DMF and then diluted with water. Bicalutamide thereupon precipitates from the solution; the product is filtered off, washed with water and dried in vacuo.

| Yield: | 3.9 g |
| --- | --- |
| Melting point: | 187°-189° C. |
| Purity: | 95.8% (HPLC) |

The invention claimed is:
1. A process for preparing N-(4"-cyano-3'-trifluoromethylphenyl)-3-(4"-fluorophenylsulfonyl)-2-hydroxy-2-methylpropionamide (bicalutamide), comprising reacting an epoxide of the general formula (I)

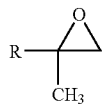

in which R is a radical of the formula (II)

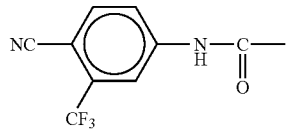

or a precursor thereof with a p-fluorophenylsulfinate salt and, if R is a precursor of the radical of the formula (II), the latter is converted into a radical of the formula (II).

2. A process for preparing N-(4'-cyano-3'-trifluoromethylphenyl)-3-(4''-fluorophenylsulfonyl)-2-hydroxy-2-methylpropionamide (bicalutamide), comprising reacting a compound of the general formula (III)

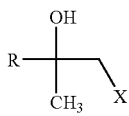

in which R is a radical of the formula (II)

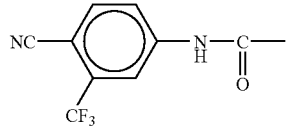

or a precursor thereof, and X is a leaving group, with a p-fluorophenylsulfinate salt and, if R is a precursor of the radical of the formula (II), the latter is converted into a radical of the formula (II).

3. The process as claimed in claim 1, in which the epoxide of the general formula (I) is obtained from a compound of the general formula (III)

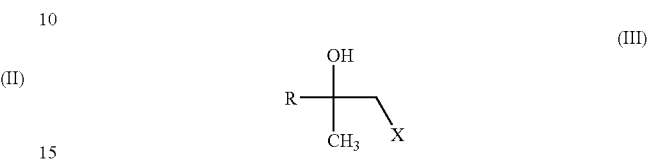

in which R is as defined in claim 1, and X is a leaving group.

4. The process as claimed in claim 3, in which the reaction is carried out starting from the compound of the general formula (III) up to the reaction with the p-fluorophenylsulfinate salt in a one-pot reaction.

5. The process as claimed in claim 1, in which the precursor for the radical of the formula (II) is a radical -COY in which Y is a group suitable for amide formation.

6. The process as claimed in claim 5, in which the radical -COY is selected from the group consisting of carboxyl, acid halides, normal esters and activated esters.

7. The process as claimed in claim 2, in which X is selected from the group consisting of halogens such as Cl, Br and I, and alkyl- and arylsulfonates such as mesylate, tosylate and brosylate.

8. The process as claimed in claim 1, in which the epoxide of the general formula (I) or the compound of the general formula (III) is employed in the form of its racemate or of one of its optically active R or S enantiomers.

9. The process as claimed in claim 1, in which the p-fluorophenylsulfinate salt is employed as alkali metal p-fluorophenylsulfinate and in particular as sodium p-fluorophenylsulfinate.

* * * * *